US009987122B2

(12) United States Patent  
Argentine

(10) Patent No.: US 9,987,122 B2  
(45) Date of Patent: Jun. 5, 2018

(54) ILIAC BRANCH DEVICE AND METHOD

(71) Applicant: Medtronic Vascular, Inc., Santa Rosa, CA (US)

(72) Inventor: Jeffery Argentine, Petaluma, CA (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 85 days.

(21) Appl. No.: 15/097,605

(22) Filed: Apr. 13, 2016

(65) Prior Publication Data

US 2017/0296324 A1 Oct. 19, 2017

(51) Int. Cl.
| | | |
|---|---|---|
| *A61F 2/07* | (2013.01) | |
| *A61F 2/844* | (2013.01) | |
| *A61F 2/06* | (2013.01) | |

(52) U.S. Cl.
CPC ............... *A61F 2/07* (2013.01); *A61F 2/844* (2013.01); *A61F 2002/065* (2013.01); *A61F 2002/075* (2013.01)

(58) Field of Classification Search
CPC ............. A61F 2/07; A61F 2/065; A61F 2/067
USPC ................................. 623/1.35–1.36
See application file for complete search history.

(56) References Cited

U.S. PATENT DOCUMENTS

| | | |
|---|---|---|
| 5,562,724 A | 10/1996 | Vorwerk et al. |
| 5,575,817 A | 11/1996 | Martin |
| 5,609,627 A | 3/1997 | Goicoechea et al. |
| 5,632,772 A | 5/1997 | Alcime et al. |
| 5,639,278 A | 6/1997 | Dereume et al. |
| 5,676,696 A | 10/1997 | Marcade |
| 5,676,697 A | 10/1997 | McDonald |
| 5,683,449 A | 11/1997 | Marcade |
| 5,855,598 A | 1/1999 | Pinchuk |
| 5,916,263 A | 6/1999 | Goicoechea et al. |
| 5,938,696 A | 8/1999 | Goicoechea et al. |
| 5,984,955 A | 11/1999 | Wisselink |
| 5,993,481 A | 11/1999 | Marcade et al. |

(Continued)

FOREIGN PATENT DOCUMENTS

| | | |
|---|---|---|
| EP | 2837362 | 2/2015 |
| EP | 2875796 | 5/2015 |

(Continued)

OTHER PUBLICATIONS

Pearce et al., "Anatomic Suitability of Aortoiliac Aneurysms for Next Generation Branched Systems" Annals of Vascular Surgery, vol. 29, No. 1, Jan. 2015.

(Continued)

*Primary Examiner* — Suzette J Gherbi

(57) ABSTRACT

An iliac branch device includes an iliac septum limb configured to be deployed in the common iliac artery. The iliac septum limb includes a graft material, a proximal end, and a septum. The graft material defines a common iliac lumen extending between the proximal end and the septum, the graft material and the septum defining an internal iliac lumen and an external iliac lumen. The iliac branch device including the iliac septum limb has several modes of adjustability. In addition, the iliac branch device has a relatively small cross-sectional area allowing the iliac branch device to treat relatively small iliac aneurysms in short common iliac arteries. This allows the iliac aneurysms to be treated at very early stages of the disease.

14 Claims, 7 Drawing Sheets

(56) References Cited

U.S. PATENT DOCUMENTS

| | | | |
|---|---|---|---|
| 6,030,415 A | 2/2000 | Chuter | |
| 6,117,167 A | 9/2000 | Goicoechea et al. | |
| 6,293,969 B1 | 9/2001 | Chuter | |
| 6,302,906 B1 | 10/2001 | Goicoechea et al. | |
| 6,344,056 B1 | 2/2002 | Dehdashtian | |
| 6,416,542 B1 | 7/2002 | Marcade et al. | |
| 6,454,796 B1 | 9/2002 | Barkman et al. | |
| 6,464,721 B1 | 10/2002 | Marcade et al. | |
| 6,592,615 B1 | 7/2003 | Marcade et al. | |
| 6,645,242 B1 | 11/2003 | Quinn | |
| 6,648,913 B1 | 11/2003 | Yee et al. | |
| 6,652,580 B1 | 11/2003 | Chuter et al. | |
| 6,660,033 B1 | 12/2003 | Marcade et al. | |
| 6,695,875 B2 | 2/2004 | Stelter et al. | |
| 6,773,454 B2 | 8/2004 | Wholey et al. | |
| 6,802,859 B1 | 10/2004 | Pazienza et al. | |
| 6,814,752 B1 | 11/2004 | Chuter | |
| 6,849,087 B1 | 2/2005 | Chuter | |
| 6,929,661 B2 | 8/2005 | Bolduc et al. | |
| 6,942,691 B1 | 9/2005 | Chuter | |
| 6,942,692 B2 | 9/2005 | Landau et al. | |
| 6,964,679 B1 | 11/2005 | Marcade et al. | |
| 6,986,751 B2 | 1/2006 | Villafana et al. | |
| 6,991,615 B2 | 1/2006 | Villafana et al. | |
| 7,011,643 B2 | 3/2006 | Villafana et al. | |
| 7,014,653 B2 | 3/2006 | Ouriel et al. | |
| 7,105,020 B2 | 9/2006 | Greenberg et al. | |
| 7,122,052 B2 | 10/2006 | Greenhalgh | |
| 7,135,037 B1 | 11/2006 | Chuter et al. | |
| 7,144,421 B2 | 12/2006 | Carpenter et al. | |
| 7,160,318 B2 | 1/2007 | Greenberg et al. | |
| 7,220,274 B1 | 5/2007 | Quinn | |
| 7,226,474 B2 | 6/2007 | Iancea et al. | |
| 7,267,685 B2 | 9/2007 | Butaric et al. | |
| 7,294,147 B2 | 11/2007 | Hartley | |
| 7,407,509 B2 | 8/2008 | Greenberg et al. | |
| 7,666,221 B2 | 2/2010 | Escano | |
| 7,674,284 B2 | 3/2010 | Melsheimer | |
| 7,708,773 B2 | 5/2010 | Pinchuk et al. | |
| 7,766,962 B1 | 8/2010 | Quinn | |
| 7,828,837 B2 | 11/2010 | Khoury | |
| 7,828,838 B2 | 11/2010 | Bolduc et al. | |
| 7,862,604 B1 | 1/2011 | Marcade et al. | |
| 7,914,572 B2 | 3/2011 | Hartley et al. | |
| 7,927,367 B2 | 4/2011 | Chuter | |
| 8,021,413 B2 | 9/2011 | Dierking et al. | |
| 8,048,140 B2 | 11/2011 | Purdy | |
| 8,092,511 B2 | 1/2012 | Chuter | |
| 8,105,372 B1 | 1/2012 | Chuter | |
| 8,177,833 B2 | 5/2012 | Chuter et al. | |
| 8,211,166 B2 | 7/2012 | Chuter et al. | |
| 8,257,430 B2 | 9/2012 | Mead | |
| 8,317,856 B2 | 11/2012 | Shalev et al. | |
| 8,337,547 B2 | 12/2012 | Iancea et al. | |
| 8,523,934 B2 | 9/2013 | Purdy | |
| 8,545,549 B2 | 10/2013 | Hartley et al. | |
| 8,551,158 B2 | 10/2013 | Roeder et al. | |
| 8,556,961 B2 | 10/2013 | Quinn | |
| 8,574,288 B2 | 11/2013 | Hartley et al. | |
| 8,628,567 B1 | 1/2014 | Chuter et al. | |
| 8,702,791 B2 | 4/2014 | Kelly | |
| 8,709,068 B2 | 4/2014 | Shalev et al. | |
| 8,734,504 B2 | 5/2014 | Kelly | |
| 8,945,200 B1 | 2/2015 | Eblacas et al. | |
| 9,320,591 B2 * | 4/2016 | Bolduc | A61B 17/00234 |
| 2006/0095119 A1 | 5/2006 | Bolduc | |
| 2006/0229707 A1 | 10/2006 | Khoury | |
| 2007/0123972 A1 | 5/2007 | Greenberg et al. | |
| 2007/0162109 A1 | 7/2007 | Davila et al. | |
| 2007/0250154 A1 | 10/2007 | Greenberg et al. | |
| 2009/0099648 A1 | 4/2009 | Yu | |
| 2012/0095547 A1 | 4/2012 | Chuter | |
| 2013/0123902 A1 | 5/2013 | Iancea et al. | |
| 2013/0218259 A1 | 8/2013 | Quinn | |
| 2013/0274850 A1 | 10/2013 | Kelly | |
| 2013/0274853 A1 | 10/2013 | Kelly | |
| 2013/0274854 A1 | 10/2013 | Kelly | |
| 2013/0274857 A1 | 10/2013 | Quinn | |
| 2013/0274861 A1 | 10/2013 | Kelly | |
| 2014/0094902 A1 | 4/2014 | Khoury | |
| 2014/0100650 A1 * | 4/2014 | Chobotov | A61F 2/07 623/1.35 |
| 2014/0172064 A1 | 6/2014 | Kelly | |
| 2014/0180394 A1 | 6/2014 | Greenberg et al. | |
| 2014/0214051 A1 * | 7/2014 | Bolduc | A61B 17/00234 606/139 |
| 2015/0057737 A1 | 2/2015 | Ondersma et al. | |
| 2015/0105850 A1 * | 4/2015 | Shahriari | A61F 2/856 623/1.13 |
| 2015/0190257 A1 * | 7/2015 | Cragg | A61F 2/07 623/1.12 |
| 2016/0354218 A1 * | 12/2016 | Shahriari | A61F 2/856 |

FOREIGN PATENT DOCUMENTS

| | | |
|---|---|---|
| EP | 2777606 | 1/2016 |
| WO | WO2013/155306 | 10/2013 |

OTHER PUBLICATIONS

PCT/US2017/026942, The International Search Report and the Written Opinion of the International Searching Authority, dated Jun. 13, 2017.

* cited by examiner

ILIAC BRANCH DEVICE AND METHOD

BACKGROUND

Field

The present application relates to an intra-vascular device and method. More particularly, the present application relates to a device for treatment of intra-vascular diseases.

Description of the Related Art

A conventional stent-graft typically includes a radially expandable reinforcement structure, formed from a plurality of annular stent rings, and a cylindrically shaped layer of graft material defining a lumen to which the stent rings are coupled. Stent-grafts are well known for use in tubular shaped human vessels.

To illustrate, endovascular aneurysmal exclusion is a method of using a stent-graft to exclude pressurized fluid flow from the interior of an aneurysm, thereby reducing the risk of rupture of the aneurysm and the associated invasive surgical intervention.

Challenges occur in patients with an iliac aneurysm. Often the short length of the common iliac artery prevents patients from receiving endovascular aneurysmal exclusion therapy to treat the iliac aneurysm.

SUMMARY

An iliac branch device includes an iliac septum limb configured to be deployed in the common iliac artery. The iliac septum limb includes a graft material, a proximal end, and a septum. The graft material defines a common iliac lumen extending between the proximal end and the septum, the graft material and the septum defining an internal iliac lumen and an external iliac lumen.

The iliac branch device including the iliac septum limb has several modes of adjustability. In addition, the iliac branch device has a relatively small cross-sectional area allowing the iliac branch device to treat relatively small iliac aneurysms in short common iliac arteries. This allows the iliac aneurysms to be treated at very early stages of the disease.

BRIEF DESCRIPTION OF DRAWINGS

Common reference numerals are used throughout the drawings and detailed description to indicate like elements.

DETAILED DESCRIPTION

As an overview and in accordance with one embodiment, an iliac branch device including an iliac septum limb has several modes of adjustability. In addition, the iliac branch device has a relatively small cross-sectional area allowing the iliac branch device to treat relatively small iliac aneurysms in short common iliac arteries. This allows the iliac aneurysms to be treated at very early stages of the disease.

Figure 1:
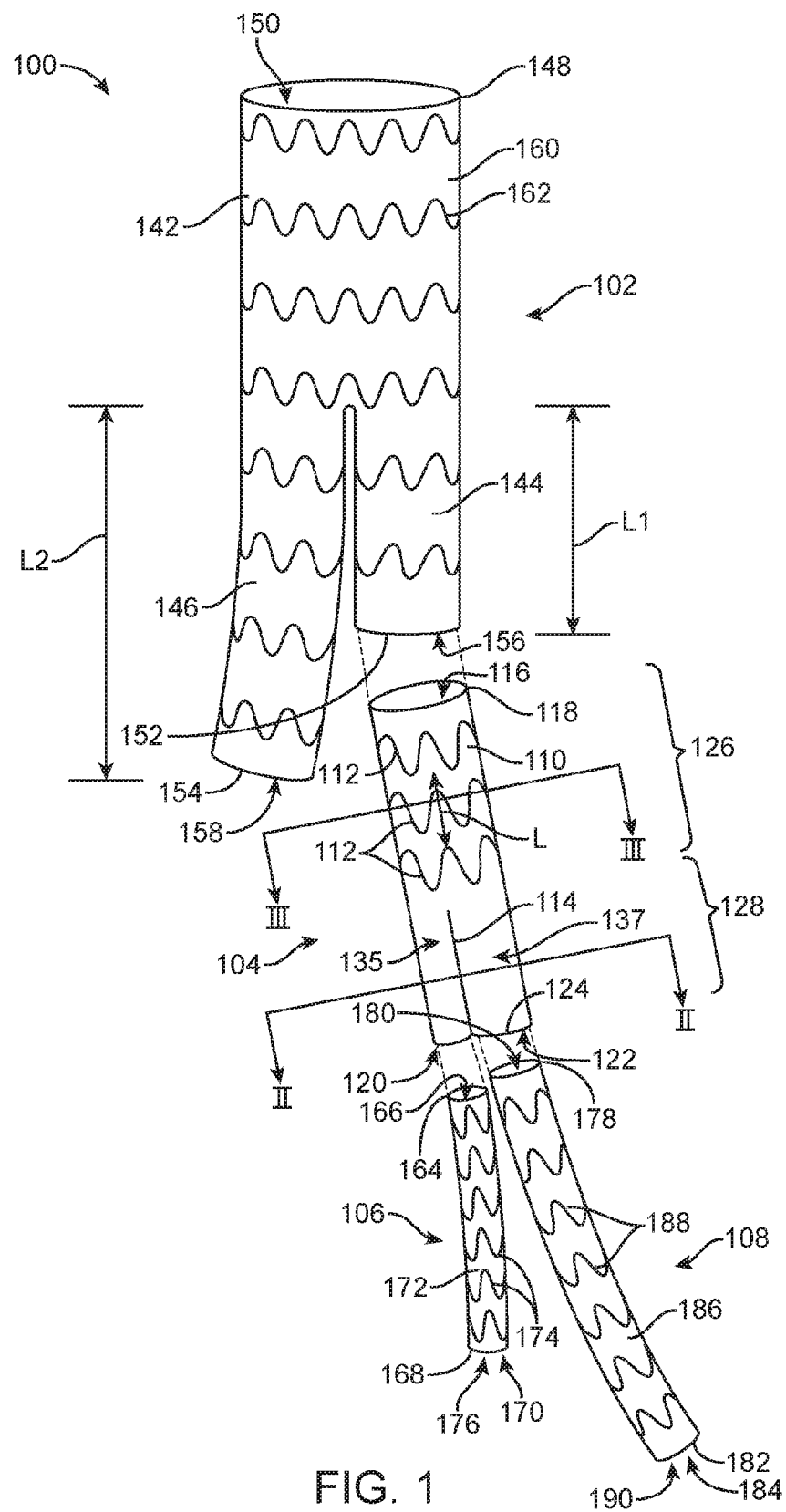
FIG. 1 is an exploded perspective view of an iliac branch device in accordance with one embodiment.
Figure 2:
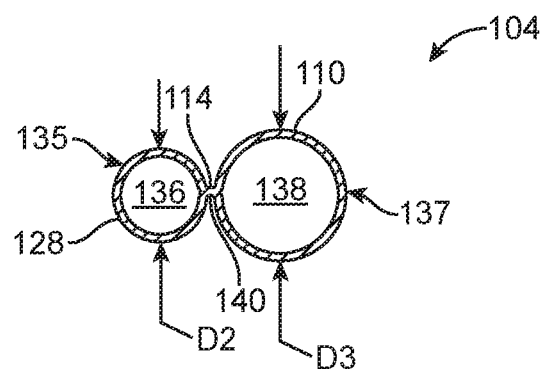
FIG. 2 is a cross-sectional view along the line II-II of an iliac septum limb of the iliac branch device of FIG. 1 in accordance with one embodiment.
Figure 3:
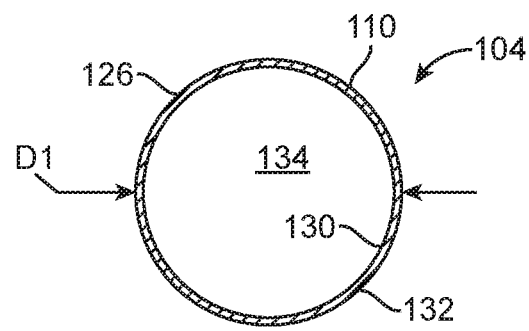
FIG. 3 is a cross-sectional view along the line III-III of the iliac septum limb of the iliac branch device of FIG. 1 in accordance with one embodiment.

Now in more detail, FIG. 1 is an exploded perspective view of an iliac branch device 100 in accordance with one embodiment. FIG. 2 is a cross-sectional view along the line II-II of an iliac septum limb 104 of iliac branch device 100 of FIG. 1 in accordance with one embodiment. FIG. 3 is a cross-sectional view along the line of iliac septum limb 104 of iliac branch device 100 of FIG. 1 in accordance with one embodiment.

Referring now to FIGS. 1, 2, and 3 together, iliac branch device 100 includes an aortic bifurcated stent graft 102, iliac septum limb 104, an internal iliac stent graft 106, and an external iliac stent graft 108.

Iliac septum limb 104 includes a graft material 110, one or more stent rings 112, and a septum 114. In accordance with this embodiment, iliac septum limb 104 includes a proximal opening 116 at a proximal end 118 of iliac septum limb 104. Iliac septum limb 104 further includes an internal iliac opening 120 and an external iliac opening 122 at a distal end 124 of iliac septum limb 104. Internal iliac opening 120 and external iliac opening 122 are sometime called distal first and second openings 120, 122, respectively.

As used herein, the proximal end of a prosthesis such as iliac septum limb 104 is the end closest to the heart via the path of blood flow whereas the distal end is the end furthest away from the heart during deployment. In contrast and of note, the distal end of the catheter is usually identified to the end that is farthest from the operator (handle) while the proximal end of the catheter is the end nearest the operator (handle).

For purposes of clarity of discussion, as used herein, the distal end of the catheter is the end that is farthest from the operator (the end furthest from the handle) while the distal end of the prosthesis is the end nearest the operator (the end nearest the handle), i.e., the distal end of the catheter and the proximal end of the stent-graft are the ends furthest from the handle while the proximal end of the catheter and the distal end of the stent-graft are the ends nearest the handle. However, those of skill in the art will understand that depending upon the access location, the stent-graft and delivery system description may be consistent or opposite in actual usage.

Iliac septum limb 104 further includes a longitudinal axis L. Iliac septum limb 104 includes a proximal section 126 and a distal section 128. Proximal section 126 extends generally parallel to longitudinal axis L between proximal end 118 and septum 114. Distal section 128, sometimes_ called a septum section 128, extends along the length of septum 114 from proximal section 126 to distal end 124.

At proximal section 126, graft material 110 is cylindrical having a substantially uniform diameter D1. However, in other embodiments, graft material 110 varies in diameter. Graft material 110 includes a cylindrical inner surface 130 and an opposite outer surface 132.

Stent rings 112 are attached to graft material 110 at proximal section 126. Illustratively, stent rings 112 are self-expanding structures, e.g., formed of nickel titanium alloy (nitinol), or other shaped memory material.

In one embodiment, graft material 110 is non-permeable, e.g., is polyester terephthalate (PET), expanded polyester terephthalate (ePET), or other non-permeable graft material. As graft material 110 is non-permeable, blood or other fluid does not pass through graft material 110.

A common iliac lumen 134 is defined by graft material 110. Common iliac lumen 134 extends generally parallel to longitudinal axis L and between proximal opening 116 and septum 114.

Septum 114 is a wall or partition dividing an internal iliac lumen 136 from an external iliac lumen 138. In one embodiment, septum 114 is formed by attaching the cylindrical graft material 110 together with an attachment structure 140. Attachment structure 140 includes stitching, adhesive, or other attachment means in various embodiments. Generally, septum 114 divides common iliac lumen 134 into internal iliac lumen 136 and external iliac lumen 138. As iliac septum limb 104 is formed from graft material 110, stent rings 112, and septum 114 as stitching in one embodiment, iliac septum limb 104 is relatively simple and has minimal associated fabrication costs.

Septum 114 divides graft material 110 into an internal iliac leg 135 and an external iliac leg 137. Internal iliac leg 135 and external iliac leg 137 are connected together by septum 114.

More particularly, graft material 110 and septum 114 define internal iliac lumen 136 within internal iliac leg 135 and external iliac lumen 138 within external iliac leg 137. Internal iliac lumen 136 extends generally parallel to longitudinal axis L and between proximal section 126 and internal iliac opening 120. External iliac lumen 138 extends generally parallel to longitudinal axis L and between proximal section 126 and external iliac opening 122. In this embodiment, internal iliac lumen 136 and external iliac lumen 138 are directly adjacent and parallel to one another and have the same length.

Internal iliac lumen 136 has a diameter D2 less than a diameter D3 of external iliac lumen 138. Diameter D1 of common iliac lumen 134 is greater than diameter D3 of external iliac lumen 138.

Common iliac lumen 134 is in fluid communication with internal iliac lumen 136 and external iliac lumen 138. Septum 114 provides a smooth transition from common iliac lumen 134 to lumens 136, 138. Accordingly, blood flow through common iliac lumen 134 flows to internal iliac lumen 136 and external iliac lumen 138 with minimal restriction. Further, in cross-sectional area, distal section 128 is less than or equal to proximal section 126. As distal section 128 does not flare out from proximal section 126, the range of anatomical applications for iliac septum limb 104 is maximized.

Aortic bifurcated stent graft 102 includes a main body 142, a short, e.g., first, leg 144, and a long, e.g., second, leg 146. An example of a suitable aortic bifurcated stent graft 102 includes the Endurant® IIs AAA stent graft manufactured by Medtronic, Minneapolis, Minn.

Main body 142 extends from a proximal end 148 of aortic bifurcated stent graft 102 to legs 144, 146. Main body 142 defines a main lumen 150. Short leg 144 extends from main body 142 to a distal end 152 of short leg 144. Long leg 146 extends from main body 142 to a distal end 154 of long leg 146. Legs 144, 146 define branch lumens 156, 158, respectively. Main lumen 150 is bifurcated into branch lumens 156, 158. Aortic bifurcated stent graft 102 includes graft material 160 and one or more stent rings 162.

A length L1 of short leg 144 is less than a length L2 of long leg 146. Proximal end 118 of iliac septum limb 104 is configured to fit within either short leg 144 or long leg 146 in one embodiment. This provides a mode of adjustment of iliac branch device 100 to accommodate variations in anatomy. More particularly, iliac septum limb 104 is configured to fit within short leg 144 in the event the common iliac artery is short or within long leg 146 in the event that the common iliac artery is longer.

In one embodiment, as described further below, stent rings 112 of iliac septum limb 104 are located within and released in either short leg 144 or long leg 146 to secure iliac septum limb 104 to aortic bifurcated stent graft 102. Iliac septum limb 104 is slideable within, e.g., can be located further in or out of, aortic bifurcated stent graft 102 giving another mode of adjustability. This further allows treatment of short common iliac arteries, e.g., among certain patient populations, particularly in Asia.

Internal iliac stent graft 106 is a tubular member including a proximal end 164 having a proximal opening 166 therein. Internal iliac stent graft 106 further includes a distal end 168 having a distal opening 170 therein. Internal iliac stent graft 106 includes a graft material 172 and one or more stent rings 174. Graft material 172 defines an internal iliac stent graft lumen 176 extending between proximal opening 166 and distal opening 170.

Proximal end 164 of internal iliac stent graft 106 is configured to fit within internal iliac leg 135 of iliac septum limb 104 in one embodiment. In one embodiment, as described further below, stent rings 174 of internal iliac stent graft 106 are located within and released in internal iliac leg 135 to secure internal iliac stent graft 106 to iliac septum limb 104.

External iliac stent graft 108 is a tubular member including a proximal end 178 having a proximal opening 180 therein. External iliac stent graft 108 further includes a distal end 182 having a distal opening 184 therein. External iliac stent graft 108 includes a graft material 186 and one or more stent rings 188. Graft material 186 defines an external iliac stent graft lumen 190 extending between proximal opening 180 and distal opening 184.

Proximal end 178 of external iliac stent graft 108 is configured to fit within external iliac leg 137 of iliac septum limb 104. In one embodiment, as described further below, stent rings 188 of external iliac stent graft 108 are located within and released in external iliac leg 137 to secure external iliac stent graft 108 to iliac septum limb 104.

The diameter of external iliac stent graft 108 is sized to match diameter D3 of external iliac lumen 138. Similarly, the diameter of internal iliac stent graft 106 is sized to match diameter D2 of internal iliac lumen 136.

Figure 4:
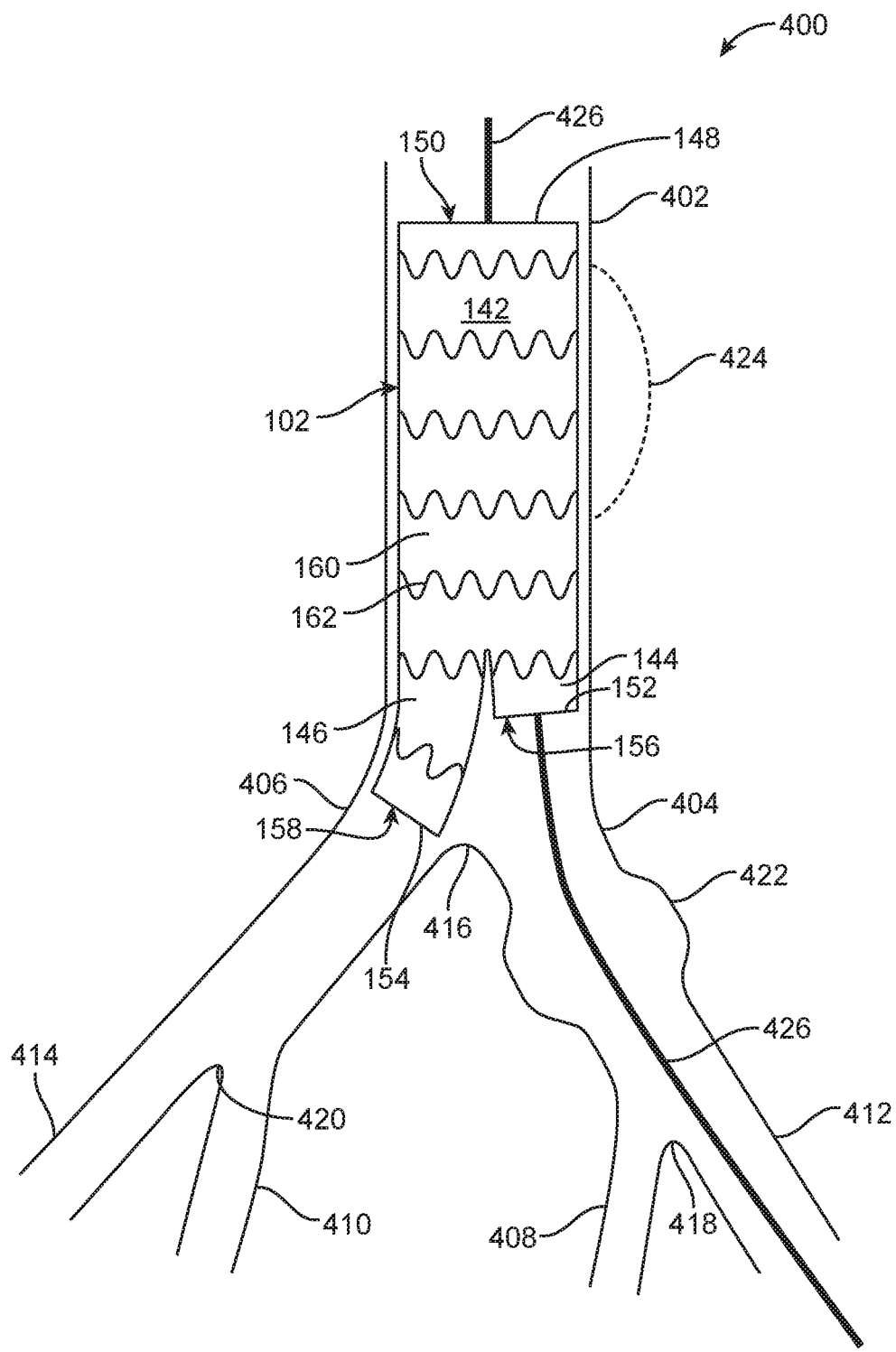
FIG. 4 is a partial cross-sectional view of a vessel assembly including an aortic bifurcated stent graft of the iliac branch device of FIG. 1 in accordance with one embodiment.

FIG. 4 is a partial cross-sectional view of a vessel assembly 400 including aortic bifurcated stent graft 102 of iliac branch device 100 of FIG. 1 in accordance with one embodiment. Vessel assembly 400 illustrates a series of vessels within the human body, including the aorta 402, the common iliac arteries 404, 406, internal iliac arteries 408, 410, and external iliac arteries 412, 414. More particularly, the aorta 402 descends to an aortic bifurcation 416 from which extends common iliac arteries 404, 406. Common iliac artery 404 descends to a common iliac artery bifurcation 418 from which extends internal iliac artery 408 and external iliac artery 412. Similarly, common iliac artery 406 descends to a common iliac artery bifurcation 420 from which extends internal iliac artery 410 and external iliac artery 414.

In accordance with this example, common iliac artery 404 includes an aneurysm 422, i.e., a diseased section of tissue.

Aortic bifurcated stent graft 102 is deployed within aorta 402. For example, the introduction of aortic bifurcated stent graft 102 is preceded by placement of a guidewire 426, e.g., via the femoral artery via a femoral incision (not shown). Aortic bifurcated stent graft 102 is deployed such that main body 142, short leg 144, and long leg 146 are located within aorta 402.

Generally, aortic bifurcated stent graft 102 operates as an anchor to secure iliac septum limb 104 in place as discussed further below. In one embodiment, aorta 402 includes an aneurysm 424. In accordance with this embodiment, aortic bifurcated stent graft 102 excludes aneurysm 424. However, in another embodiment, aorta 402 is healthy, i.e., does not include an aneurysm.

Figure 5:
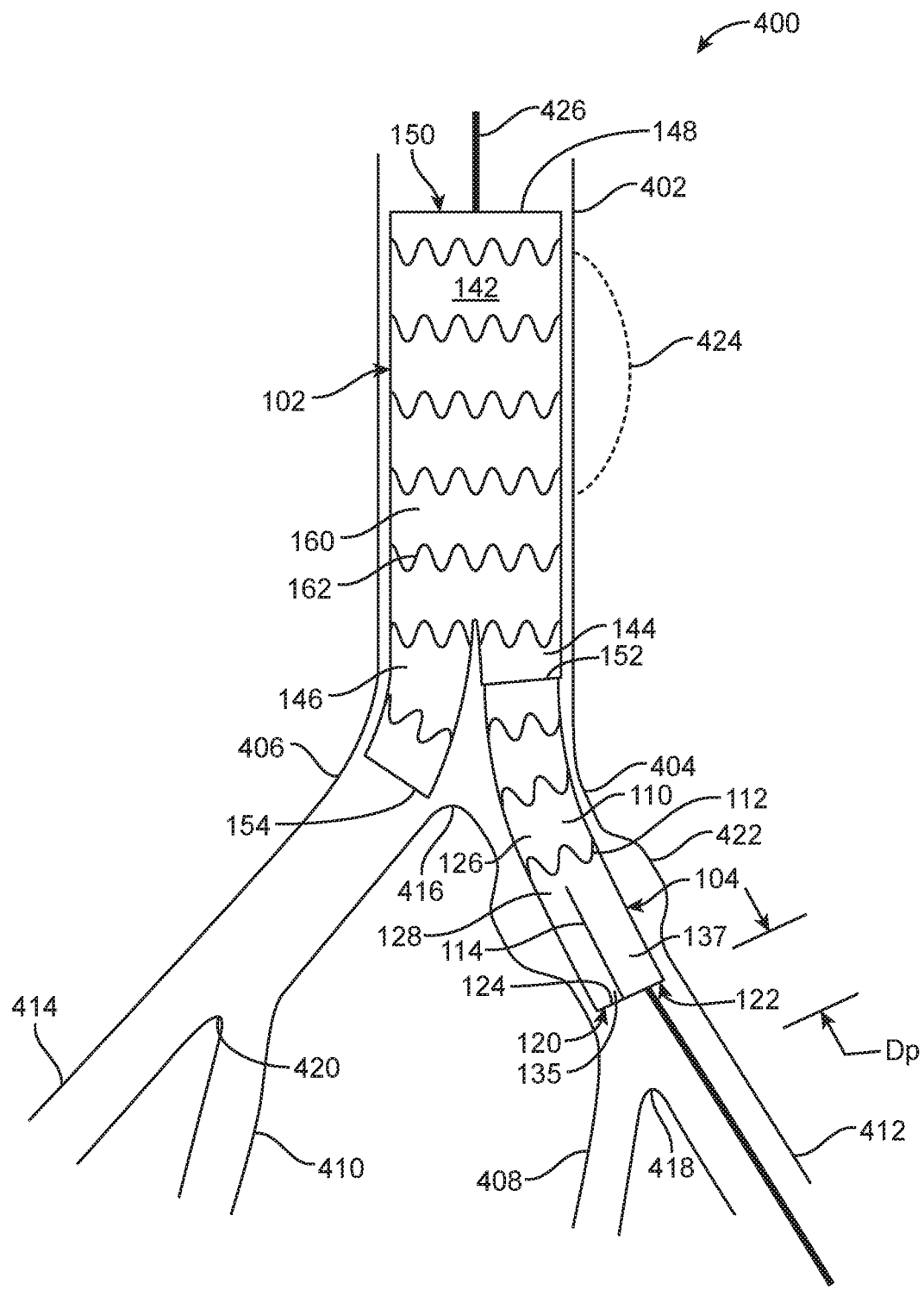
FIG. 5 is a partial cross-sectional view of the vessel assembly of FIG. 4 at a later stage of deployment of the iliac branch device of FIG. 1 in accordance with one embodiment.

FIG. 5 is a partial cross-sectional view of vessel assembly 400 of FIG. 4 at a later stage of deployment of iliac branch device 100 of FIG. 1 in accordance with one embodiment. Referring now to FIG. 5, iliac septum limb 104 is deployed within short leg 144 of aortic bifurcated stent graft 102. Illustratively, iliac septum limb 104 is advanced on guide wire 426 to be located within short leg 144. Stent ring(s) 112 are released to self expand into short leg 144 thus securing iliac septum limb 104 to aortic bifurcated stent graft 102.

Iliac septum limb 104 is deployed such that distal end 124 is located a predefined distance Dp from common iliac bifurcation 418. In one embodiment, predefined distance Dp is 10 millimeters (mm) although predefined distance Dp is other distances in other embodiments. As discussed above, iliac septum limb 104 is slideable in and out of aortic bifurcated stent graft 102 to position distal end 124 predefined distance Dp from common iliac bifurcation 418. This adjustability allows treatment of short common iliac arteries, e.g., among certain patient populations, particularly in Asia.

As the distal end 124 is placed predefined distance Dp above common iliac bifurcation 418, the only necessary variable in iliac septum limb 104 is diameter D1, D2, D3 (see FIGS. 2-3). Further, as the overall diameter of iliac septum limb 104 is relatively small and does not flare out, iliac septum limb 104 can be used to treat small aneurysms, e.g., aneurysm 422 is 1.5 times the natural diameter of common iliac artery 404. In various embodiments, iliac septum limb 104 can be deployed in common iliac artery 404 having a small diameter, e.g., 28 mm, 24 mm, 20 mm, and generally, 16 mm or larger. This allows treatment of aneurysm 422 at the early stages of the disease.

However, in the event that a greater length is necessary, aortic bifurcated stent graft 102 can be deployed such that long leg 146 is deployed to cooperate with common iliac artery 404 and short leg is deployed to cooperate with common iliac artery 406, i.e., rotated 180°. Iliac septum limb 104 is then deployed within long leg 146. This gives another mode of adjustability.

Figure 6:
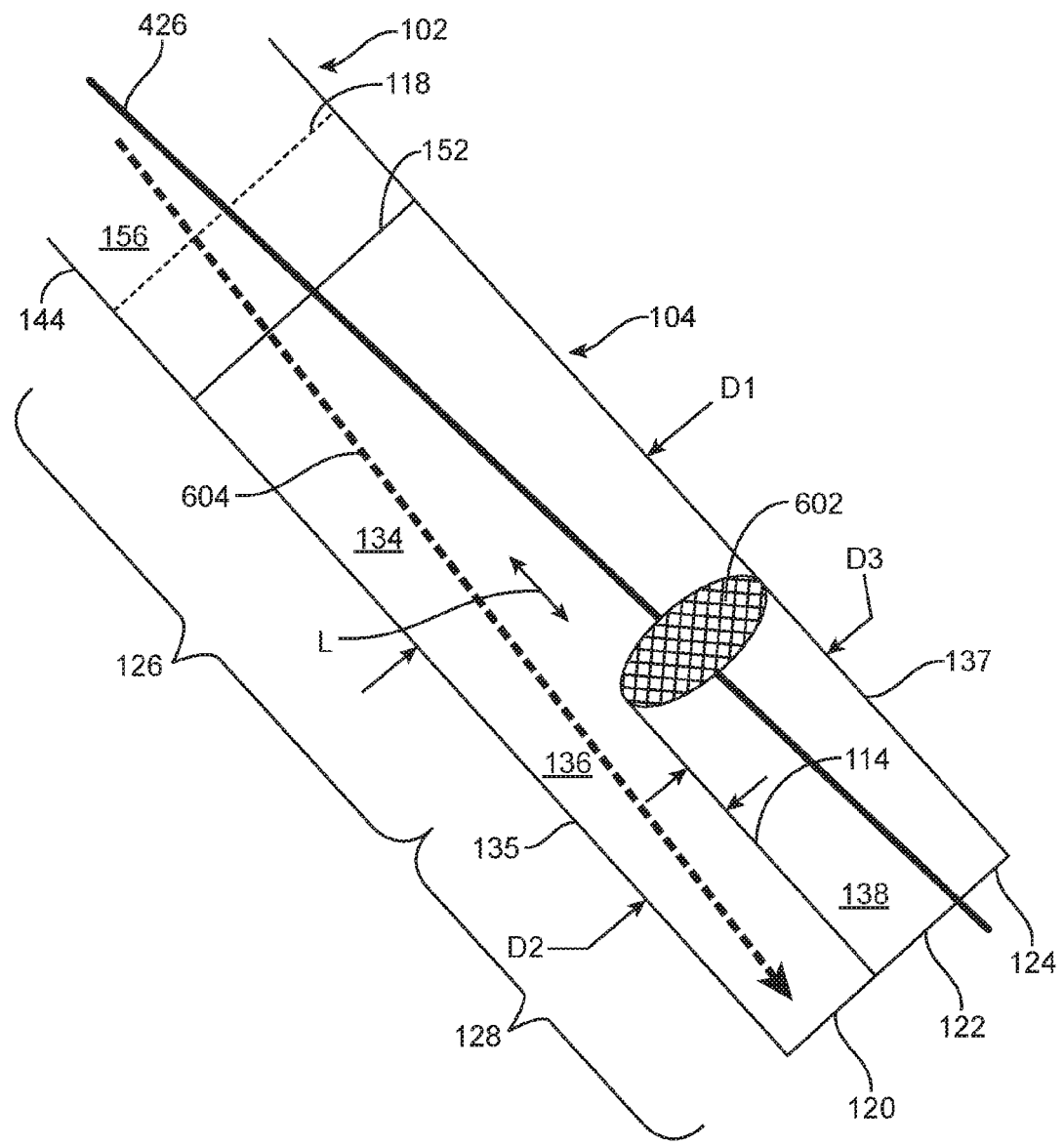
FIG. 6 is a cross-sectional view of the aortic bifurcated stent graft having the iliac septum limb deployed therein in accordance with one embodiment.

FIG. 6 is a cross-sectional view of aortic bifurcated stent graft 102 having iliac septum limb 104 deployed therein in accordance with one embodiment. Referring now to FIGS. 5 and 6 together, after deployment of iliac septum limb 104 within aortic bifurcated stent graft 102, an occlusion balloon 602 is advanced, e.g., on guidewire 426, and deployed, e.g., inflated, within external iliac leg 137 of iliac septum limb 104.

Typically, internal iliac artery 408 cannot be practically accessed from its distal end. Accordingly, balloon 602 is deployed as a guide for a second guidewire 604 (indicated as a dashed line). More particularly, second guidewire 604 is introduced brachially and proximally into proximal section 126, exits internal iliac leg 135, and enters internal iliac artery 408. In another embodiment, second guidewire 604 is introduced from the opposite femoral artery. Balloon 602 insures that the path of second guide wire 604 leads into internal iliac leg 135 and internal iliac artery 408. Balloon 602 is then deflated and removed.

Figure 7:
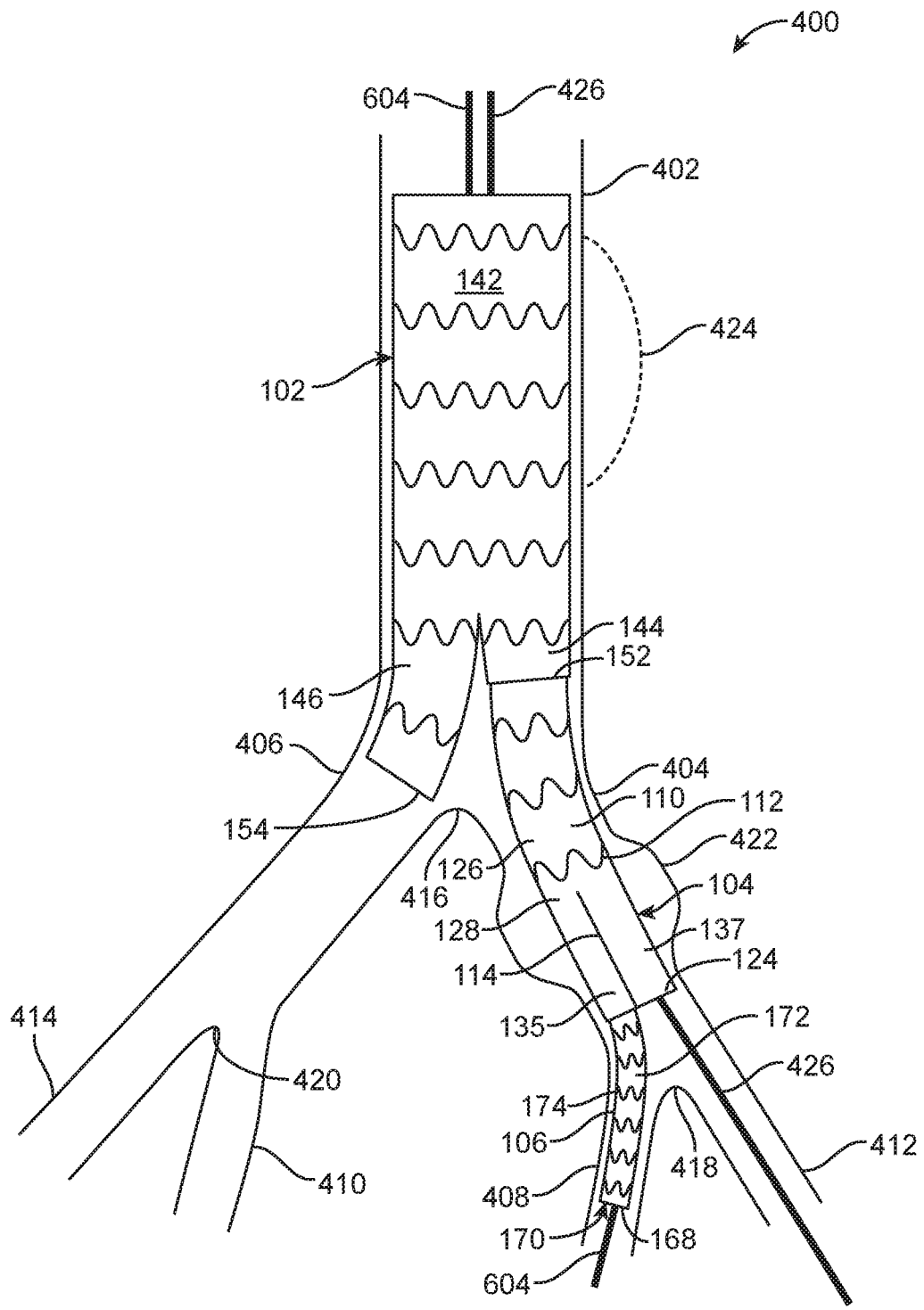
FIG. 7 is a partial cross-sectional view of the vessel assembly of FIG. 5 at a later stage of deployment of the iliac branch device of FIG. 1 in accordance with one embodiment.

FIG. 7 is a partial cross-sectional view of vessel assembly 400 of FIG. 5 at a later stage of deployment of iliac branch device 100 of FIG. 1 in accordance with one embodiment. Referring now to FIG. 7, internal iliac stent graft 106 is advanced over second guidewire 604 and into internal iliac artery 408. Stent ring(s) 174 of internal iliac stent graft 106 are release to self expand into internal iliac leg 135 of iliac septum limb 104. This secures internal iliac stent graft 106 to iliac septum limb 104 and to healthy tissue within internal iliac artery 408.

Figure 8:
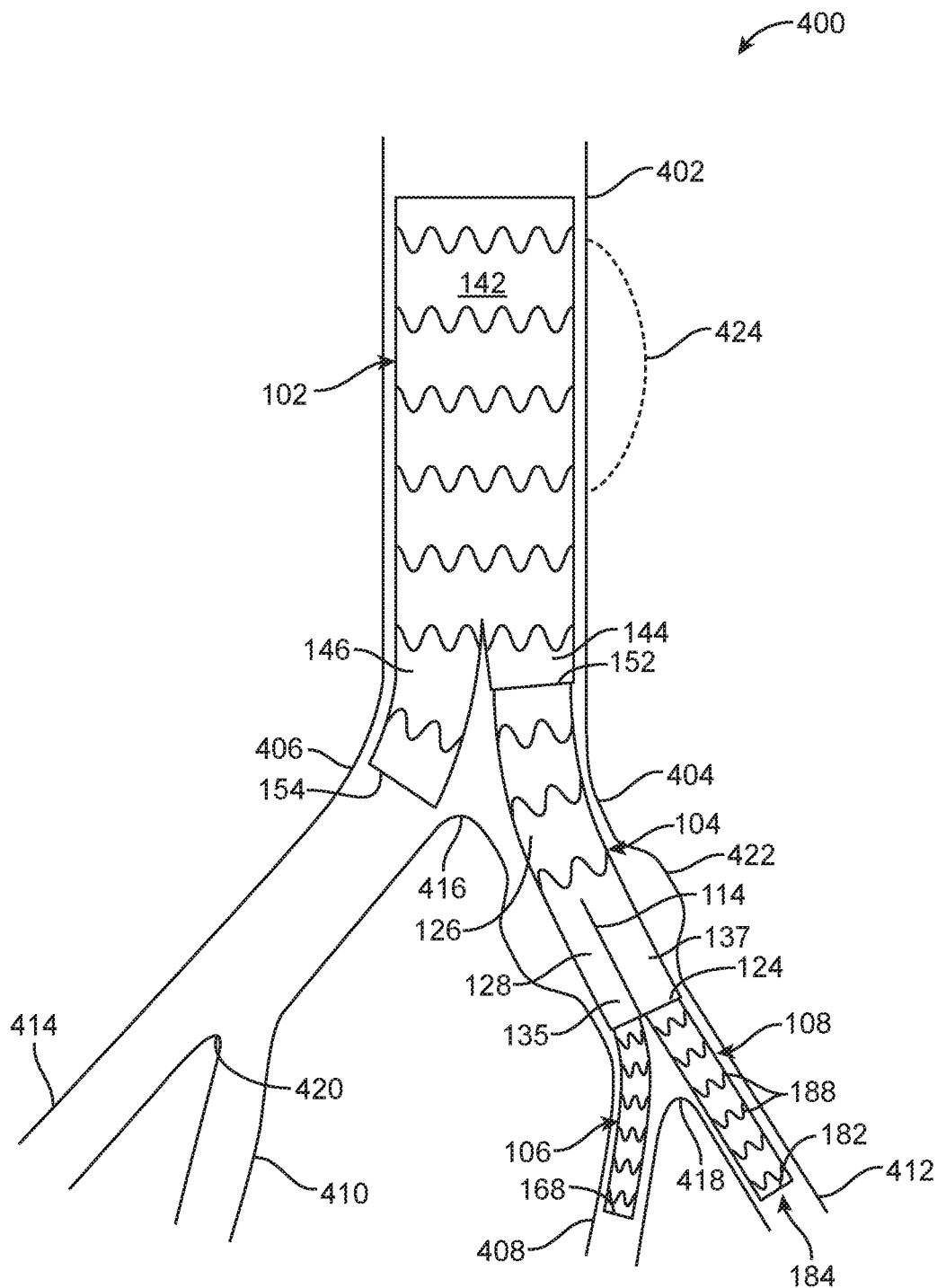
FIG. 8 is a partial cross-sectional view of the vessel assembly of FIG. 7 at a later stage of deployment of the iliac branch device of FIG. 1 in accordance with one embodiment.

FIG. 8 is a partial cross-sectional view of vessel assembly 400 of FIG. 7 at a later stage of deployment of iliac branch device 100 of FIG. 1 in accordance with one embodiment. Referring now to FIGS. 7 and 8 together, second guidewire 604 is removed. External stent graft 108 is advanced over guidewire 426 into external iliac artery 412. Stent ring(s) 188 of external iliac stent graft 108 are release to self expand into external iliac leg 137 of iliac septum limb 104. This secures external iliac stent graft 108 to iliac septum limb 104 and to healthy tissue within external iliac artery 412. Guidewire 426 is then removed completing deployment of iliac branch device 100 and exclusion of aneurysm 422 of common iliac artery 404. Specifically, iliac branch device 100 bridges from healthy vessel to healthy vessel insuring that aneurysm 422 is excluded. In one embodiment, a stent graft is deployed within long leg 146 and into common iliac artery 406 to insure perfusion of common iliac artery 406.

This disclosure provides exemplary embodiments. The scope is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. An iliac branch device comprising:
   an iliac septum limb configured to be deployed in the common iliac artery, the iliac septum limb comprising:
      a graft material;
      a proximal end;
      a septum, wherein the graft material defines a common iliac lumen extending between the proximal end and the septum, the graft material and the septum defining an internal iliac lumen and an external iliac lumen; and
   an internal iliac stent graft coupled within internal iliac lumen; and
   an external iliac stent graft coupled within the external iliac lumen.

2. The iliac branch device of claim 1 further comprising:
   an attachment structure attaching the graft material together to create the septum.

3. The iliac branch device of claim 2 wherein the attachment structure comprises stitching.

4. The iliac branch device of claim 1 wherein a diameter of the internal iliac lumen is less than a diameter of the external iliac lumen.

5. The iliac branch device of claim 4 wherein a diameter of the common iliac lumen is greater than the diameter of the external iliac lumen.

6. The iliac branch device of claim 1 wherein the iliac septum limb further comprises a self-expanding structure attached to the graft material at the proximal end.

7. The iliac branch device of claim 6 further comprising an aortic bifurcated stent graft comprising a first distal leg and a second distal leg, the self-expanding structure coupling the iliac septum limb inside of the first distal leg.

8. The iliac branch device of claim 7 wherein the first distal leg is shorter than the second distal leg.

9. A method of deploying an iliac branch device comprising:
deploying an aortic bifurcated stent graft into the aorta;
deploying a proximal end of an iliac septum limb into a first distal leg of the aortic bifurcated stent graft, wherein the deploying the proximal end comprises spacing a distal end of the iliac septum limb a predefined distance above a bifurcation of an internal iliac artery and an external iliac artery;
deploying an internal iliac stent graft within an internal iliac lumen of the iliac septum limb; and
deploying an external iliac stent graft within an external iliac lumen of the iliac septum limb; and
deploying an occlusion balloon within the external iliac lumen prior to the deploying the internal iliac stent graft.

10. A method of deploying an iliac branch device comprising:
deploying an aortic bifurcated stent graft into the aorta; and
deploying a proximal end of an iliac septum limb into a first distal leg of the aortic bifurcated stent graft, wherein the deploying the proximal end comprises spacing a distal end of the iliac septum limb a predefined distance above a bifurcation of an internal iliac artery and an external iliac artery, wherein the predefined distance is 10 millimeters (mm).

11. The method of claim 9 wherein the aortic bifurcated stent graft further comprises a second distal leg.

12. The method of claim 11 wherein the first distal leg is shorter than the second distal leg.

13. The method of claim 9 wherein a diameter of the internal iliac stent graft is less than a diameter of the external iliac stent graft.

14. The method of claim 9 further comprising removing the occlusion balloon after the deploying the internal iliac stent graft.

* * * * *